(12) United States Patent
Sawutz et al.

(10) Patent No.: US 7,485,650 B2
(45) Date of Patent: Feb. 3, 2009

(54) HIGH AFFINITY LIGANDS FOR NOCICEPTIN RECEPTOR ORL-1

(75) Inventors: David G. Sawutz, Maplewood, NJ (US); Philippe Brianceau, Millsboro, DE (US); Ana Bercovici, West Orange, NJ (US); Ginny D. Ho, Murray Hill, NJ (US); Deen Tulshian, Lebanon, NJ (US)

(73) Assignee: Schering Corporation, Kenilworth, NJ (US)

( * ) Notice: Subject to any disclaimer, the term of this patent is extended or adjusted under 35 U.S.C. 154(b) by 192 days.

(21) Appl. No.: 11/259,765

(22) Filed: Oct. 27, 2005

(65) Prior Publication Data

US 2006/0217414 A1    Sep. 28, 2006

Related U.S. Application Data

(60) Continuation-in-part of application No. 10/761,977, filed on Jan. 21, 2004, now Pat. No. 7,094,784, which is a division of application No. 10/155,277, filed on May 23, 2002, now Pat. No. 6,716,846, which is a division of application No. 09/769,824, filed on Jan. 25, 2001, now Pat. No. 6,455,527, which is a division of application No. 09/359,771, filed on Jul. 26, 1999, now Pat. No. 6,262,066.

(60) Provisional application No. 60/094,240, filed on Jul. 27, 1998.

(51) Int. Cl.
*A61K 31/46* (2006.01)

(52) U.S. Cl. ....................... 514/304; 546/132

(58) Field of Classification Search ................. 546/132; 514/304

See application file for complete search history.

(56) References Cited

U.S. PATENT DOCUMENTS

| 6,262,066 | B1 * | 7/2001 | Tulshian et al. ............. 514/299 |
| 7,094,784 | B2 * | 8/2006 | Tulshian et al. ............. 514/249 |
| 2001/0011092 | A1 | 8/2001 | Tulshian et al. |
| 2006/0217414 | A1 | 9/2006 | Sawutz et al. |

OTHER PUBLICATIONS

PCT International Search Report for PCT/US2006/041714 dated Mar. 22, 2007.

* cited by examiner

*Primary Examiner*—Deepak Rao
(74) *Attorney, Agent, or Firm*—Krishna G. Banerjee

(57) ABSTRACT

The compound of the formula

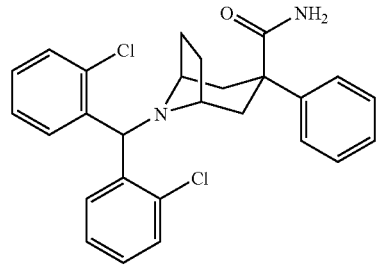

or a pharmaceutically acceptable salt or solvate thereof, pharmaceutical compositions therefore, and the use of said compounds as nociceptin receptor inhibitors useful in the treatment of anxiety are disclosed.

4 Claims, No Drawings

HIGH AFFINITY LIGANDS FOR NOCICEPTIN RECEPTOR ORL-1

CROSS REFERENCE TO RELATED APPLICATIONS

This application is a continuation-in-part of U.S. Ser. No. 10/761,977, filed Jan. 21, 2004 now U.S. Pat. No. 7,094,784, which is a divisional of U.S. Ser. No. 10/155,277, filed May 23, 2002, now U.S. Pat. No. 6,716,846, which is a divisional of U.S. Ser. No. 09/769,824, filed Jan. 25, 2001, now U.S. Pat. No. 6,455,527, which is a divisional of U.S. Ser. No. 09/359,771 filed Jul. 26, 1999, now U.S. Pat. No. 6,262,066, which claims the benefit of U.S. Provisional Application No. 60/094,240, filed Jul. 27, 1998.

BACKGROUND

The nociceptin receptor ORL-1 has been shown to be involved with modulation of pain in animal models. ORL-1 (the nociceptin receptor) was discovered as an "orphan opioid-like receptor" i.e. a receptor whose ligand was unknown. The nociceptin receptor is a G protein coupled receptor. While highly related in structure to the three classical opioid receptors, i.e. the targets for traditional opioid analgesics, it is not activated by endogenous opioids. Similarly, endogenous opioids fail to activate the nociceptin receptor. Like the classical opioid receptors, the nociceptin receptor has a broad distribution in the central nervous system.

In late 1995, nociceptin was discovered and shown to be an endogenous peptide ligand that activates the nociceptin receptor. Data included in the initial publications suggested that nociceptin and its receptor are part of a newly discovered pathway involved in the perception of painful stimuli. Subsequent work from a number of laboratories has shown that nociceptin, when administered intraspinally to rodents, is an analgesic. The efficacy of nociceptin is similar to that of endogenous opioid peptides. Recent data has shown that nociceptin acts as an axiolytic when administered directly into the brain of rodents. When tested in standard animals models of anxiety, the efficacy of nociceptin is similar to that seen with classical benzodiazapine anxiolytics. These data suggest that a small molecule agonist of the nociceptin receptor could have significant analgesic or anxiolytic activity.

Additional recent data (Rizzi, et al, *Life Sci.*, 64, (1999), p. 157-163) has shown that the activation of nociceptin receptors in isolated guinea pig bronchus inhibits tachykinergic non adrenergic-non cholinergic contraction, indicating that nociceptin receptor agonists could be useful in the treatment of asthma. Also, it has been reported (Ciccocioppo et al, *Physchpharmacology*, 141 (1999), p. 220-224) nociceptin reduces the rewarding properties of ethanol in msP alcohol preferring rats, suggesting that intervention of nociceptin could be useful in the treatment of alcohol abuse. In EP 856,514, 8-substituted 1,3,8-triazaspiro[4,5]decan-4-on derivatives were disclosed as agonists and/or antagonists of orphanin FQ (i.e., nociceptin) useful in the treatment of various disorders, including depression; 2-oxoimidazole derivatives disclosed in WO98/54168 were described as having similar utility. Earlier, benzimidazolyl piperidines were disclosed in U.S. Pat. No. 3,318,900 as having analgesic activity.

Potent analgesic agents such as traditional opioids, e.g. morphine, carry with them significant side-effects. Clinically relevant side-effects include tolerance, physical dependence, respiratory depression and a decrease in gastrointestinal motility. For many patients, particularly those subjected to chronic opioid therapy, i.e. cancer patients, these side effects limit the dose of opioid that can be administered. Clinical data suggests that more than one-third of cancer patients have pain which is poorly controlled by present agents. Data obtained with nociceptin suggest the potential for advantages over opioids. When administered chronically to rodents, nociceptin, in contrast to morphine, showed no addiction liability. Additionally, chronic morphine treatment did not lead to a "cross-tolerance" to nociceptin, suggesting that these agents act via distinct pathways.

In view of the current interest in pain relief, a welcome contribution to the art would be additional compounds useful for modifying the effect of nociceptin, a natural ligand to ORL-1 and therefore useful in the management of pain and anxiety. Such a contribution is provided by this invention.

SUMMARY OF THE INVENTION

Compounds of the present invention are represented by formula I

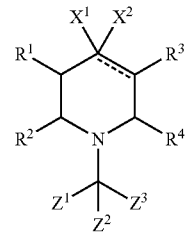

or a pharmaceutically acceptable salt or solvate thereof, wherein:

the dotted line represents an optional double bond;

$X^1$ is $R^5$—$(C_1$-$C_{12})$alkyl, $R^6$—$(C_3$-$C_{12})$cycloalkyl, $R^7$-aryl, $R^8$-heteroaryl or $R^{10}$—$(C_3$-$C_7)$heterocycloalkyl;

$X^2$ is —CHO, —CN, —NHC(=$NR^{26}$)$NHR^{26}$, —CH(=$NOR^{26}$), —$NHOR^{26}$, $R^7$-aryl, $R^7$-aryl($C_1$-$C_6$)alkyl, $R^7$-aryl($C_1$-$C_6$)alkenyl, $R^7$-aryl($C_1$-$C_6$)-alkynyl, —$(CH_2)_v$$OR^{13}$, —$(CH_2)_v$$COOR^{27}$, —$(CH_2)_v$$CONR^{14}R^{15}$, —$(CH_2)_v$$NR^{21}R^{22}$ or —$(CH_2)_v$$NHC(O)R^{21}$, wherein v is zero, 1, 2 or 3 and wherein q is 1 to 3 and a is 1 or 2;

or $X^1$ is

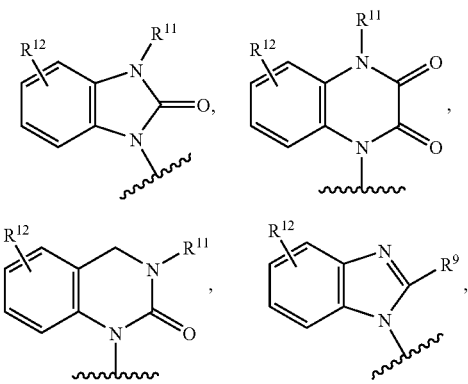

-continued

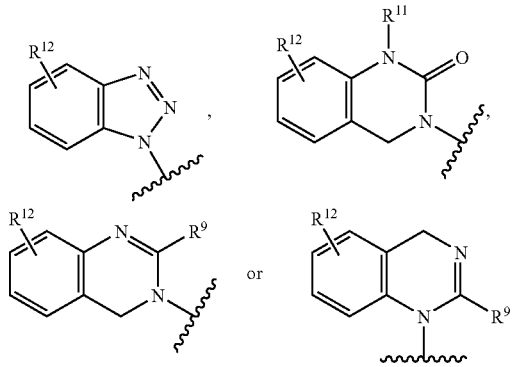

and $X^2$ is hydrogen;

or $X^1$ and $X^2$ together form a spiro group of the formula

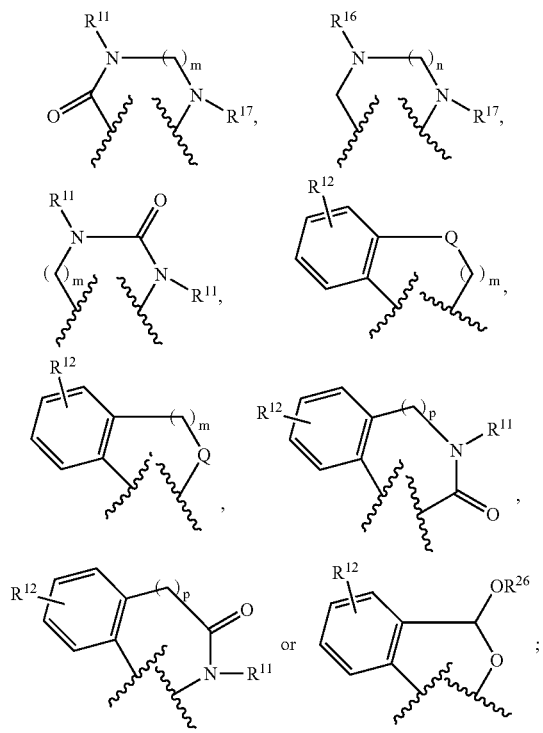

m is 1 or 2;

n is 1, 2 or 3, provided that when n is 1, one of $R^{16}$ and $R^{17}$ is —C(O)$R^{28}$;

p is 0 or 1;

Q is —CH$_2$—, —O—, —S—, —SO—, —SO$_2$—or —NR$^{17}$—;

$R^1$, $R^2$, $R^3$ and $R^4$ are independently selected from the group consisting of hydrogen and (C$_1$-C$_6$)alkyl, or ($R^1$ and $R^4$) or ($R^2$ and $R^3$) or ($R^1$ and $R^3$) or ($R^2$ and $R^4$) together can form an alkylene bridge of 1 to 3 carbon atoms;

$R^5$ is 1 to 3 substituents independently selected from the group consisting of H, $R^7$-aryl, $R^6$—(C$_3$-C$_{12}$)cycloalkyl, $R^8$-heteroaryl, $R^{10}$—(C$_3$-C$_7$)heterocycloalkyl, —NR$^{19}$R$^{20}$, —OR$^{13}$ and —S(O)$_{0-2}$R$^{13}$;

$R^6$ is 1 to 3 substituents independently selected from the group consisting of H, (C$_1$-C$_6$)alkyl, $R^7$-aryl, —NR$^{19}$R$^{20}$, —OR$^{13}$ and —SR$^{13}$;

$R^7$ is 1 to 3 substituents independently selected from the group consisting of hydrogen, halo, (C$_1$-C$_6$)alkyl, $R^{25}$-aryl, (C$_3$-C$_{12}$)cycloalkyl, —CN, —CF$_3$, —OR$^{19}$, —(C$_1$-C$_6$)alkyl-OR$^{19}$, —OCF$_3$, —NR$^{19}$R$^{20}$, —(C$_1$-C$_6$)alkyl-NR$^{19}$R$^{20}$, —NHSO$_2$R$^{19}$, —SO$_2$N(R$^{26}$)$_2$, —SO$_2$NR$^{19}$, —SOR$^{19}$, —SR$^{19}$, —NO$_2$, —CONR$^{19}$R$^{20}$, —NR$^{20}$COR$^{19}$, —COR$^{19}$, —COCF$_3$, —OCOR$^{19}$, —OCO$_2$R$^{19}$, —COOR$^{19}$, —(C$_1$-C$_6$)alkyl-NHCOOC(CH$_3$)$_3$, —(C$_1$-C$_6$)alkyl-NHCOCF$_3$, —(C$_1$-C$_6$)alkyl-NHSO$_2$—(C$_1$-C$_6$)alkyl, —(C$_1$-C$_6$)alkyl-NH-CONH—(C$_1$-C$_6$)-alkyl or

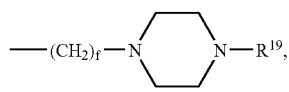

wherein f is 0 to 6; or $R^7$ substituents on adjacent ring carbon atoms may together form a methylenedioxy or ethylenedioxy ring;

$R^8$ is 1 to 3 substituents independently selected from the group consisting of hydrogen, halo, (C$_1$-C$_6$)alkyl, $R^{25}$-aryl, (C$_3$-C$_{12}$)cycloalkyl, —CN, —CF$_3$, —OR$^{19}$, —(C$_1$-C$_6$)alkyl-OR$^{19}$, —OCF$_3$, —NR$^{19}$R$^{20}$, —(C$_1$-C$_6$)alkyl-NR$^{19}$R$^{20}$, —NHSO$_2$R$^{19}$, —SO$_2$N(R$^{26}$)$_2$, —NO$_2$, —CONR$^{19}$R$^{20}$, —NR$^{20}$COR$^{19}$, —COR$^{19}$, —OCOR$^{19}$, —OCO$_2$R$^{19}$ and —COOR$^{19}$;

$R^9$ is hydrogen, (C$_1$-C$_6$)alkyl, halo, —OR$^{19}$, —NR$^{19}$R$^{20}$, —NHCN, —SR$^{19}$ or —(C$_1$-C$_6$)alkyl-NR$^{19}$R$^{20}$;

$R^{10}$ is H, (C$_1$-C$_6$)alkyl, —OR$^{19}$, —(C$_1$-C$_6$)alkyl-OR$^{19}$, —NR$^{19}$R$^{20}$ or —(C$_1$-C$_6$)alkyl-NR$^{19}$R$^{20}$;

$R^{11}$ is independently selected from the group consisting of H, $R^5$—(C$_1$-C$_6$)alkyl, $R^6$—(C$_3$-C$_{12}$)cycloalkyl, —(C$_1$-C$_6$)alkyl(C$_3$-C$_{12}$)cycloalkyl, —(C$_1$-C$_6$)alkyl-OR$^{19}$, —(C$_1$-C$_6$)alkyl-NR$^{19}$R$^{20}$ and

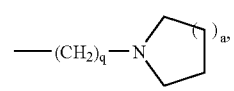

wherein q and a are as defined above;

$R^{12}$ is H, (C$_1$-C$_6$)alkyl, halo, —NO$_2$, —CF$_3$, —OCF$_3$, —OR$^{19}$, —(C$_1$-C$_6$)alkyl-OR$^{19}$, —NR$^{19}$R$^{20}$ or —(C$_1$-C$_6$)alkyl-NR$^{19}$R$^{20}$;

$R^{13}$ is H, (C$_1$-C$_6$)alkyl, $R^7$-aryl, —(C$_1$-C$_6$)alkyl-OR$^{19}$, —(C$_1$-C$_6$)alkyl-NR$^{19}$R$^{20}$; —(C$_1$-C$_6$)alkyl-SR$^{19}$; or aryl (C$_1$-C$_6$) alkyl;

$R^{14}$ and $R^{15}$ are independently selected from the group consisting of H, $R^5$—(C$_1$-C$_6$)alkyl, $R^7$-aryl and

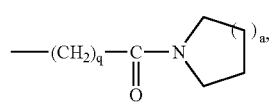

wherein q and a are as defined above;

$R^{16}$ and $R^{17}$ are independently selected from the group consisting of hydrogen, $R^5$—(C$_1$-C$_6$)alkyl, $R^7$-aryl, (C$_3$-C$_{12}$)cycloalkyl, $R^8$-heteroaryl, $R^8$-heteroaryl(C$_1$-C$_6$)alkyl, —C(O)R$^{28}$, —(C$_1$-C$_6$)alkyl(C$_3$-C$_7$)-heterocycloalkyl, —(C$_1$-C$_6$)alkyl-OR$^{19}$ and —(C$_1$-C$_6$)alkyl-SR$^{19}$;

R$^{19}$ and R$^{20}$ are independently selected from the group consisting of hydrogen, (C$_1$-C$_6$)alkyl, (C$_3$-C$_{12}$)cycloalkyl, aryl and aryl(C$_1$-C$_6$)alkyl;

R$^{21}$ and R$^{22}$ are independently selected from the group consisting of hydrogen, (C$_1$-C$_6$)alkyl, (C$_3$-C$_{12}$)cycloalkyl, (C$_3$-C$_{12}$)cycloalkyl(C$_1$-C$_6$)alkyl, (C$_3$-C$_7$)heterocycloalkyl, —(C$_1$-C$_6$)alkyl(C$_3$-C$_7$)-heterocycloalkyl, R$^7$-aryl, R$^7$-aryl (C$_1$-C$_6$)alkyl, R$^8$-heteroaryl(C$_1$-C$_{12}$)alkyl, —(C$_1$-C$_6$)alkyl-OR$^{19}$, —(C$_1$-C$_6$)alkyl-NR$^{19}$R$^{20}$, —(C$_1$-C$_6$)alkyl-SR$^{19}$, —(C$_1$-C$_6$)alkyl-NR$^{18}$—(C$_1$-C$_6$)alkyl-O—(C$_1$-C$_6$)alkyl and —(C$_1$-C$_6$)alkyl-NR$^{18}$—(C$_1$-C$_6$)alkyl-NR$^{18}$—(C$_1$-C$_6$)alkyl;

R$^{18}$ is hydrogen or (C$_1$-C$_6$)alkyl;

Z$^1$ is R$^5$—(C$_1$-C$_{12}$)alkyl, R$^7$-aryl, R$^8$-heteroaryl, R$^6$—(C$_3$-C$_{12}$)cyclo-alkyl, R$^{10}$—(C$_3$-C$_7$)heterocycloalkyl, —CO$_2$(C$_1$-C$_6$)alkyl, CN or —C(O)NR$^{19}$R$^{20}$; Z$^2$ is hydrogen or Z$^1$; Z$^3$ is hydrogen or (C$_1$-C$_6$)alkyl; or Z$^1$, Z$^2$ and Z$^3$, together with the carbon to which they are attached, form the group

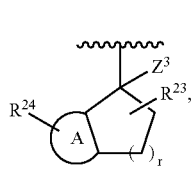 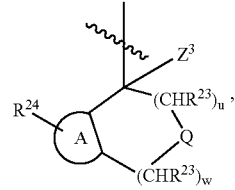

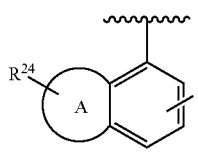 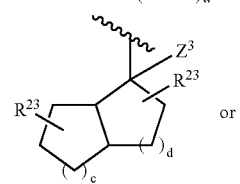

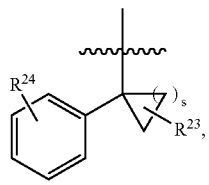

wherein r is 0 to 3; w and u are each 0-3, provided that the sum of w and u is 1-3; c and d are independently 1 or 2; s is 1 to 5; and ring A is a fused R$^7$-phenyl or R$^8$-heteroaryl ring;

R$^{23}$ is 1 to 3 substituents independently selected from the group consisting of H, (C$_1$-C$_6$)alkyl, —OR$^{19}$, —(C$_1$-C$_6$) alkyl-OR$^{19}$, —NR$^{19}$R$^{20}$ and —(C$_1$-C$_6$)alkyl-NR$^{19}$R$^{20}$;

R$^{24}$ is 1 to 3 substituents independently selected from the group consisting of R$^{23}$, —CF$_3$, —OCF$_3$, NO$_2$ or halo, or R$^{24}$ substituents on adjacent ring carbon atoms may together form a methylenedioxy or ethylenedioxy ring;

R$^{25}$ is 1-3 substituents independently selected from the group consisting of H, (C$_1$-C$_6$)alkyl, (C$_1$-C$_6$)alkoxy and halo;

R$^{26}$ is independently selected from the group consisting of H, (C$_1$-C$_6$)alkyl and R$^{25}$—C$_6$H$_4$—CH$_2$—;

R$^{27}$ is H, (C$_1$-C$_6$)alkyl, R$^7$-aryl(C$_1$-C$_6$)alkyl, or (C$_3$-C$_{12}$) cycloalkyl;

R$^{28}$ is (C$_1$-C$_6$)alkyl, —(C$_1$-C$_6$)alkyl(C$_3$-C$_{12}$)cycloalkyl, R$^7$-aryl, R$^7$-aryl-(C$_1$-C$_6$)alkyl, R$^8$-heteroaryl, —(C$_1$-C$_6$) alkyl-NR$^{19}$R$^{20}$, —(C$_1$-C$_6$)alkyl-OR$^{19}$ or —(C$_1$-C$_6$)alkyl-SR$^{19}$;

provided that when X$^1$ is

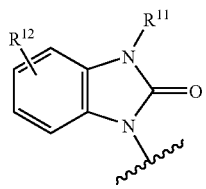

or X$^1$ and X$^2$ together are

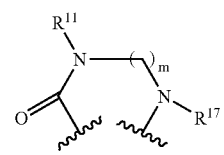

and Z$^1$ is R$^7$-phenyl, Z$^2$ is not hydrogen or (C$_1$-C$_3$)alkyl;

provided that when Z$^1$, Z$^2$ and Z$^3$, together with the carbon to which they are attached, form

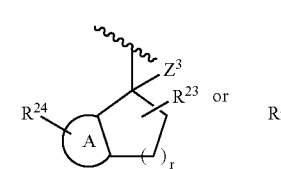 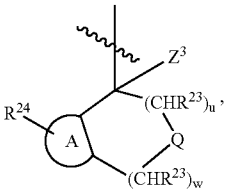

and X$^1$ and X$^2$ together are

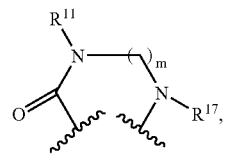

R$^{11}$ is not H, (C$_1$-C$_6$)alkyl, (C$_1$-C$_6$)alkoxy(C$_1$-C$_6$)alkyl or (C$_1$-C$_6$)hydroxyalkyl;

provided that when R$^2$ and R$^4$ form an alkylene bridge, Z$^1$, Z$^2$ and Z$^3$, together with the carbon to which they are attached, are not

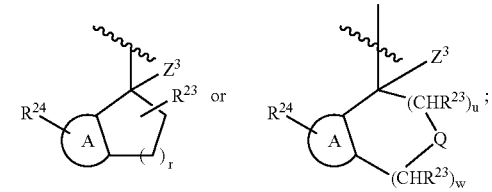

and provided that when $X^1$ is

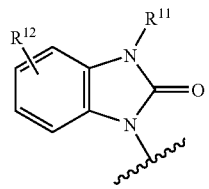

and $Z^1$ is $R^6$—($C_3$-$C_{12}$)-cycloalkyl, $Z^2$ is not H.

In another aspect, the invention relates to a pharmaceutical composition comprising a compound of formula I and a pharmaceutically acceptable carrier.

The compounds of the present invention are agonists and/or antagonists of the ORL-1 receptor, and therefore, in another aspect, the invention relates to a method of treating pain, anxiety, cough, asthma, alcohol abuse or depression, comprising administering to a mammal in need of such treatment an effective amount of a compound of formula I.

DETAILED DESCRIPTION OF THE INVENTION

The preferred compound of the invention is

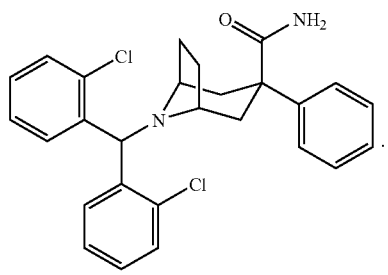

The preferred compound is useful in treating anxiety in mammals, i.e. humans and other non-human mammals including domestic animals (such as dogs and cats), livestock (such as horses, cattle, swine and sheep), and wild animals (such as those living in zoos and wildlife parks), and in non-mammalian species such as aquatic (e.g., fish and crustaceans) and avian species (poultry such as chickens, turkeys, ducks and geese, and exotic birds such as parrots). The compound is useful, for example, in treating anxiety in domestic animals that are caused by stressful situations such as being separated from their owners for boarding or transportation (i.e., separation anxiety), moving to a new home, and exposure to adverse environmental conditions (e.g., exposure to loud noises such as thunder or fireworks). The compounds are also useful for treating anxiety in livestock or wild animals, for example during transport or under various husbandry conditions. Similarly, the compound can treat anxiety in aquatic species caused by crowding in sea cages and during transport, and in avian species caused by crowding or during transport.

The compound of the formula

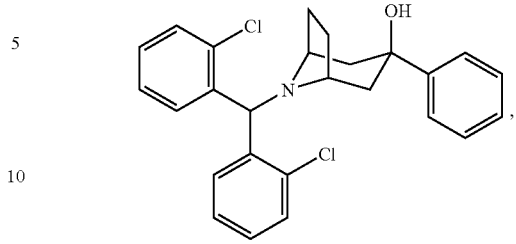

generically described above in formula I and claimed in U.S. Pat. No. 6,262,066, is also useful in treating anxiety.

As used herein, the following terms are used as defined below unless otherwise indicated:

$M^+$ represents the molecular ion of the molecule in the mass spectrum and $MH^+$ represents the molecular ion plus hydrogen of the molecule in the mass spectrum;

Bu is butyl; Et is ethyl; Me is methyl; and Ph is phenyl;

alkyl (including the alkyl portions of alkoxy, alkylamino and dialkylamino) represents straight and branched carbon chains containing from 1 to 12 carbon atoms or 1 to 6 carbon atoms; for example methyl, ethyl, propyl, iso-propyl, n-butyl, t-butyl, n-pentyl, isopentyl, hexyl and the like;

alkenyl represents an alkyl chain of 2 to 6 carbon atoms comprising one or two double bonds in the chain, e.g., vinyl, propenyl or butenyl;

alkynyl represents an alkyl chain of 2 to 6 carbon atoms comprising one triple bond in the chain, e.g., ethynyl or propynyl;

alkoxy represents an alkyl moiety covalently bonded to an adjacent structural element through an oxygen atom, for example, methoxy, ethoxy, propoxy, butoxy, pentoxy, hexoxy and the like;

aryl (including the aryl portion of arylalkyl) represents a carbocyclic group containing from 6 to 15 carbon atoms and having at least one aromatic ring (e.g., aryl is phenyl), wherein said aryl group optionally can be fused with aryl, ($C_3$-$C_7$)cycloalkyl, heteroaryl or hetero($C_3$-$C_7$)cycloalkyl rings; and wherein $R^7$-aryl means that any of the available substitutable carbon and nitrogen atoms in said aryl group and/or said fused ring(s) is optionally and independently substituted, and wherein the aryl ring is substituted with 1-3 $R^7$ groups. Examples of aryl groups are phenyl, naphthyl and anthryl;

arylalkyl represents an alkyl group, as defined above, wherein one or more hydrogen atoms of the alkyl moiety have been substituted with one to three aryl groups; wherein aryl is as defined above;

aryloxy represents an aryl group, as defined above, wherein said aryl group is covalently bonded to an adjacent structural element through an oxygen atom, for example, phenoxy;

cycloalkyl represents saturated carbocyclic rings of from 3 to 12 carbon atoms, preferably 3 to 7 carbon atoms; wherein $R^6$-cycloalkyl means that any of the available substitutable carbon atoms in said cycloalkyl group is optionally and independently substituted, and wherein the cycloalkyl ring is substituted with 1-3 $R^6$ groups;

cycloalkylalkyl represents an alkyl group, as defined above, wherein one or more hydrogen atoms of the alkyl moiety have been substituted with one to three cycloalkyl groups, wherein cycloalkyl is as defined above;

halo represents fluoro, chloro, bromo and iodo;

heteroaryl represents cyclic groups having one to three heteroatoms selected from O, S and N, said heteroatom(s) interrupting a carbocyclic ring structure and having a sufficient number of delocalized pi electrons to provide aromatic character, with the aromatic heterocyclic groups containing from 5 to 14 carbon atoms, wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted, and wherein the heteroaryl ring can be substituted with 1-3 $R^8$ groups; representative heteroaryl groups can include, for example, furanyl, thienyl, imidazoyl, pyrimidinyl, triazolyl, 2-, 3- or 4-pyridyl or 2-, 3- or 4-pyridyl N-oxide wherein pyridyl N-oxide can be represented as:

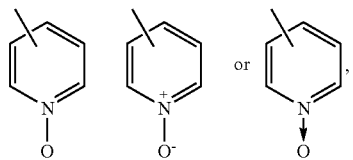

heteroarylalkyl represents an alkyl group, as defined above, wherein one or more hydrogen atoms have been replaced by one or more heteroaryl groups, as defined above;

heterocycloalkyl represents a saturated ring containing from 3 to 7 carbon atoms, preferably from 4 to 6 carbon atoms, interrupted by 1 to 3 heteroatoms selected from —O—, —S— and —$NR^{21}$—, wherein $R^{21}$ is as defined above, and wherein optionally, said ring may contain one or two unsaturated bonds which do not impart aromatic character to the ring; and wherein any of the available substitutable carbon atoms in the ring may substituted, and wherein the heterocycloalkyl ring can be substituted with 1-3 $R^{10}$ groups; representative heterocycloalkyl groups include 2- or 3-tetrahydrofuranyl, 2- or 3-tetrahydrothienyl, 1-, 2-, 3- or 4-piperidinyl, 2- or 3-pyrrolidinyl, 1-, 2- or 3-piperizinyl, 2- or 4-dioxanyl, morpholinyl,

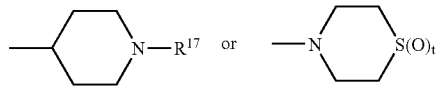

wherein $R^{17}$ is as defined above and t is 0, 1 or 2.

When the optional double bond in the piperidinyl ring of formula I is present, one of $X^1$ and $X^2$ forms the bond with the 3-position carbon and the remaining $X^1$ or $X^2$ is not hydrogen.

When $X^1$ and $X^2$ form a spiro group as defined above, the wavy lines in the structures shown in the definition indicate the points of attachment to to the 4-position carbon of the piperidinyl ring, e.g., compounds of the following formulas are formed:

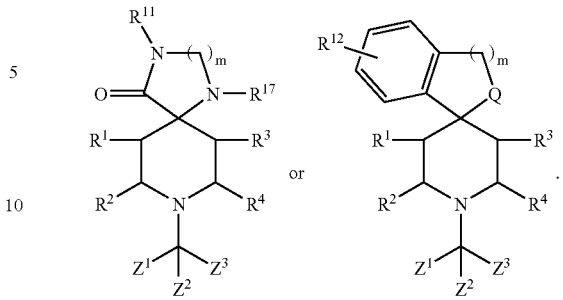

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

Compounds of the invention can be prepared by known methods from starting materials either known in the art or prepared by methods known in the art. Examples of general procedures and specific preparative examples are given below.

Typically, $X^1,X^2$-substituted piperidines are alkylated with $Z^1,Z^2,Z^3$-substituted halomethanes in the presence of excess bases such as $K_2CO_3$ and $Et_3N$, in solvents such as DMF, THF or $CH_3CN$, at room temperature or at elevated temperatures.

$X^1,X^2$-substituted piperidines are either commercially available or made by known procedures. For example, 4-hydroxy-4-phenyl-piperidine can be converted to a 4-tBoc-amino-4-phenylpiperidine according to the following reaction scheme, wherein Bn is benzyl, Ph is phenyl and tBoc is t-butoxycarbonyl:

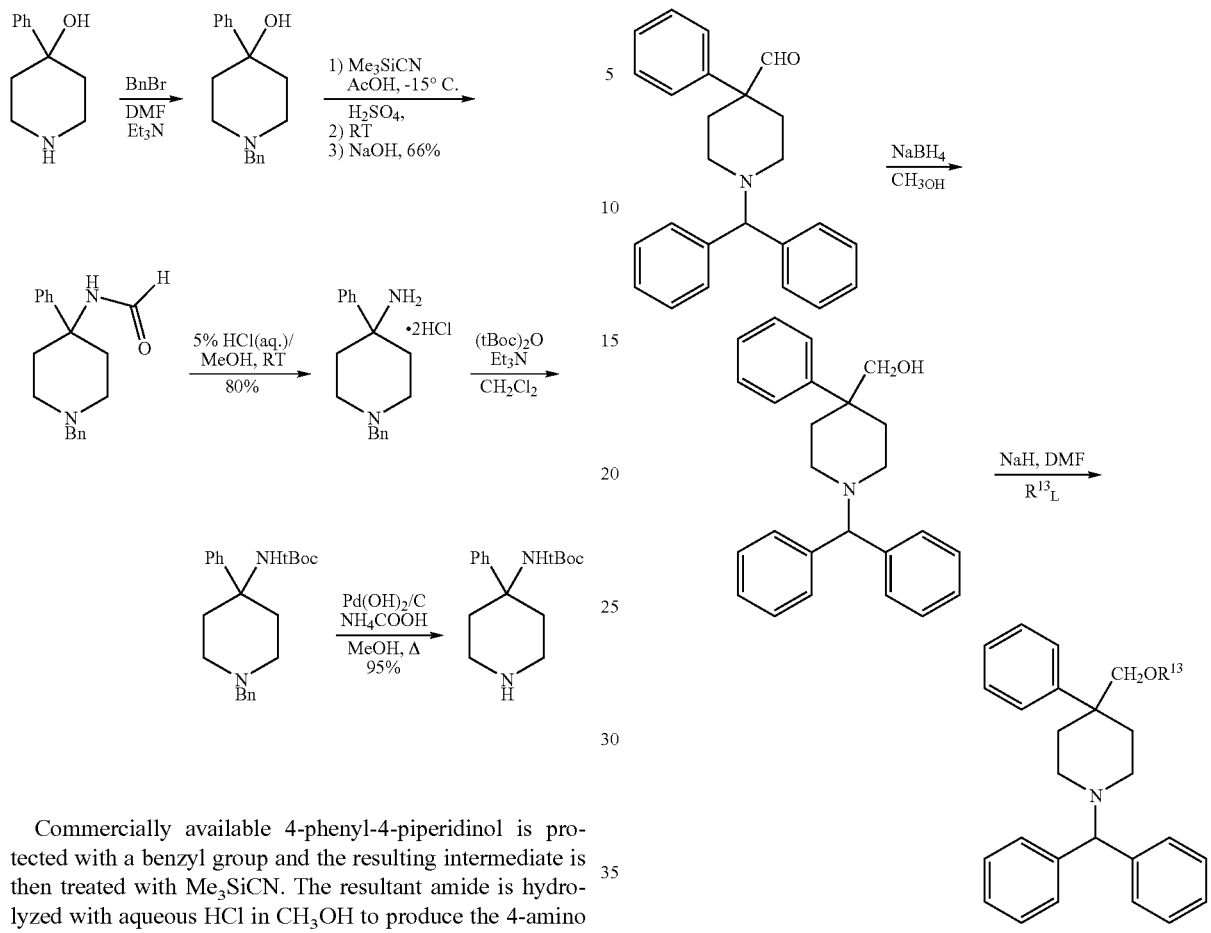

Commercially available 4-phenyl-4-piperidinol is protected with a benzyl group and the resulting intermediate is then treated with Me$_3$SiCN. The resultant amide is hydrolyzed with aqueous HCl in CH$_3$OH to produce the 4-amino compound. The amino group is protected with tBoc and the N-benzyl group is removed by hydrogenolysis to produce the desired 4-amino-piperidine derivative.

The 4-(protected)amino-piperidine then can be reacted with a $Z^1,Z^2,Z^3$-halomethane and the protecting group removed. The amine (i.e., $X^2$ is —NH$_2$) can undergo various standard conversions to obtain amine derivatives. For example, the amine of formula I can be reacted with a $R^{22}$-carboxaldehyde in the presence of a mild reducing agent such as Na(OAc)$_3$BH or with a compound of the formula $R^{22}$-L, wherein L is a leaving group such as Cl or Br, in the presence of a base such as Et$_3$N.

An alternative method for preparing compounds of formula I wherein $X^1$ is $R^7$-aryl and $X^2$ is OH involves alkylating a 4-piperidone hydrochloride with a $Z^1,Z^2,Z^3$-halomethane, then reacting the ketone with an appropriately substituted $R^7$-phenylmagnesium bromide or with a compound of the formula $X^1$-$L^1$, wherein $L^1$ is Br or I, and n-butyl-lithium.

$X^1,X^2$-substituted compounds of formula I can be converted into other compounds of formula I by performing reactions well known in the art on the $X^1$ and/or $X^2$ substituents. For example, a carboxaldehyde-substituted piperidine (i.e., $X^2$ is —CHO) can be converted to a substituted piperidine wherein $X^2$ is $R^{13}$—O—CH$_2$—, as shown in the following procedure for a compound of formula I wherein $X^1$ is phenyl, $Z^1$ and $Z^2$ are each phenyl, and $R^1$, $R^2$, $R^3$ and $R^4$, and $Z^3$ are H:

A cyano-substituted piperidine (i.e., $X^2$ is —CN) can be converted to a substituted piperidine wherein $X^2$ is $R^{21}R^{22}$N—CH$_2$— or $X^2$ is $R^{28}$C(O)NH—CH$_2$—, as shown in the following procedure for a compound of formula I wherein $X^1$ is phenyl, $R^{21}$, $R^1$, $R^2$, $R^3$ and $R^4$, and $Z^3$ are H, and L is a leaving group such as Cl or Br:

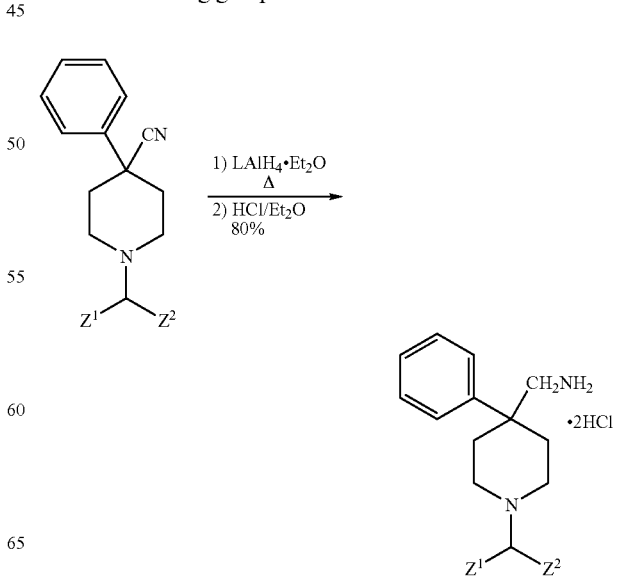

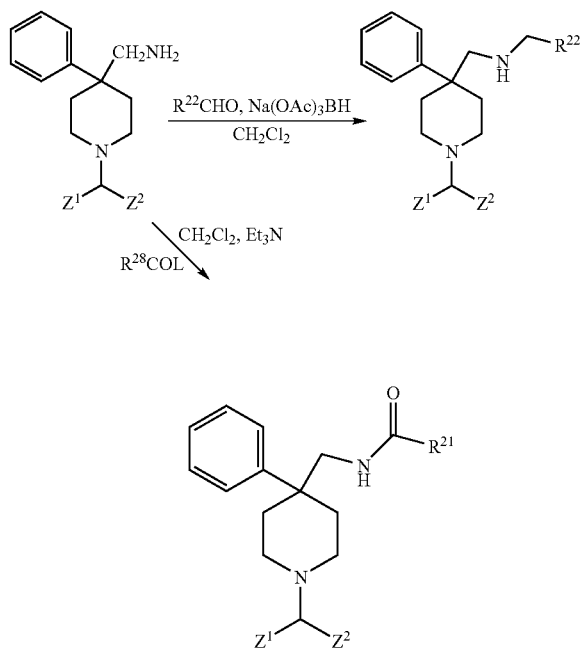

Compounds of formula I wherein $X^1$ is a benzofused nitrogen-containing heterocycle having an $R^{11}$ substituent other than hydrogen are prepared by reacting the corresponding compounds wherein $R^{11}$ is hydrogen with a compound of the formula $R^{11}L$ ($R^{11}$ is not H, and L is as defined above).

Alternatively, $X^1,X^2$-substituted piperidine starting materials can be converted into other $X^1,X^2$-substituted piperidines by similar procedures before reacting with the $Z^1,Z^2,Z^3$-substituted halomethane.

For compounds of formula I wherein $R^1$, $R^2$, $R^3$ and $R^4$ variously form alkylene bridges, commercially available N-protected 4-piperidones are treated with phenyl lithium and resulting intermediate is deprotected to produce the desired compounds, for example:

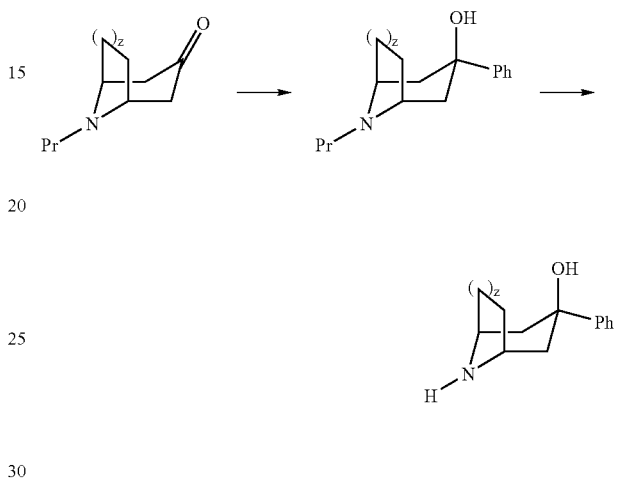

wherein Pr is a N-protecting group, Ph is phenyl and z is 1-2.

The $Z^1,Z^2,Z^3$-halomethyl derivatives wherein $Z^1$ and $Z^2$ are $R^7$-phenyl are either commercially available or can be prepared using the procedure shown in the following reaction scheme:

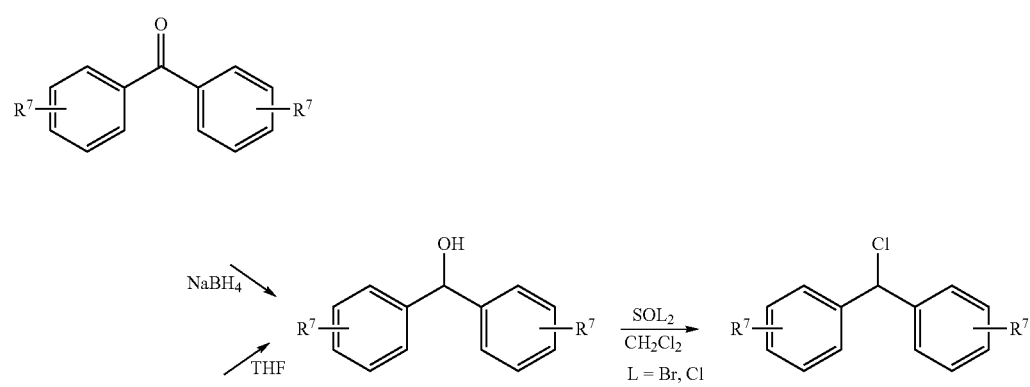

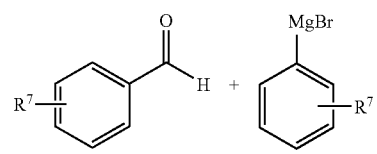

Similar procedures, or others known in the art, can be used to prepare compounds wherein the Z substituents are other than phenyl.

Preparation of the preferred compounds of the present invention and preparative starting materials thereof, are exemplified by the following examples, which should not be construed as limiting the scope of the disclosure.

The following solvents and reagents are referred to herein by the abbreviations indicated: tetrahydrofuran (THF); ethanol (EtOH); methanol (MeOH); ethyl acetate (EtOAc); N,N-dimethylformamide (DMF); dichloro-ethane (DCE); and diethyl ether (Et$_2$O). Room temperature is abbreviated as rt.

EXAMPLE 1

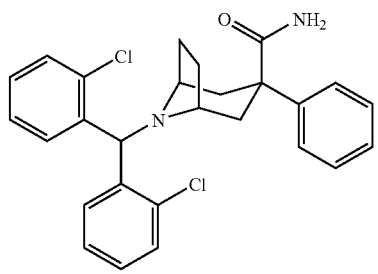

Step 1:

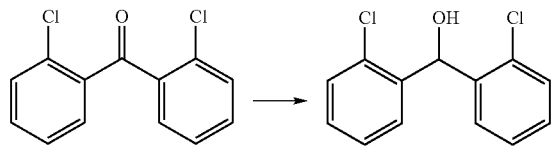

NaBH$_4$ (1.5 g, 39.82 mmol) was added to a solution of 2,2'-dichlorobenzophenone (5 g, 19.9 mmol) in MeOH (40 ml) at rt. After stirring at rt for 2 h, the mixture was quenched with H$_2$O and neutralized with 1N HCl, followed by evaporation of MeOH. The residue was extracted with EtOAc, washed with brine, dried (MgSO$_4$) and concentrated to give the desired compound 2 (5 g) as white solid which was used for the next step reaction without purification. $^1$H NMR (CDCl$_3$) δ 7.45 (m, 4H), 7.35 (m, 4H), 6.60 (d, 1H), 2.58 (d, 1H, OH).

Step 2:

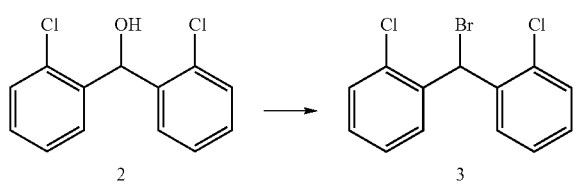

The product of Step 1 (20.36 g, 80.47 mmol) in CH$_2$Cl$_2$ was treated with SOBr$_2$ (30.11 g, 144.85 mmol) at 0° C. After stirring at rt overnight, the mixture was quenched with ice and NaHCO$_3$ (aq.), extracted with CH$_2$Cl$_2$, dried, filtered and concentrated to produce the desired compound 3 (23.6 g). $^1$H NMR (CDCl$_3$) δ 7.6 (d, 2H), 7.4 (d, 2H), 7.13 (m, 4H), 7.0 (s, 1H).

Step 3:

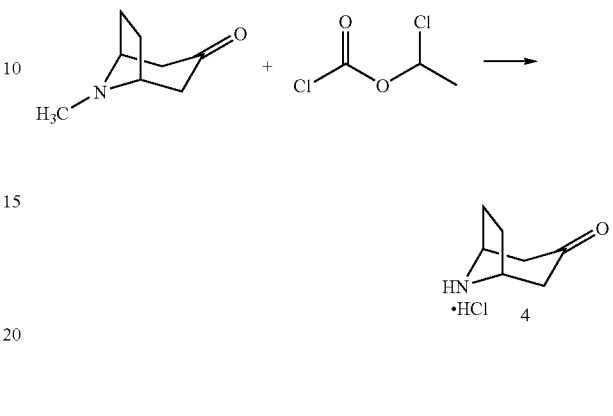

A solution of tropinone (10 g, 71.84 mmol) in DCE (200 ml) was added α-chloroethyl chloroformate (15.4 g, 108 mmol) dropwise at 0° C. The mixture was then heated at reflux for 2 h. Solvent was evaporated to give a brown residue. The residue was dissolved in MeOH (200 ml) and heated at reflux for 2 h. The MeOH was evaporated to give a solid which was stirred in EtOAc, filtered and washed with Et$_2$O to give the desired compound 4 (7 g). Crude product was used for the next step reaction without further purification. $^1$H NMR (CDCl$_3$) δ 4.45 (s, br, 2H), 3.35 (dd, 2H), 2.58 (d, 2H), 2.49 (dd, 2H), 2.0 (m, 2H).

Step 4:

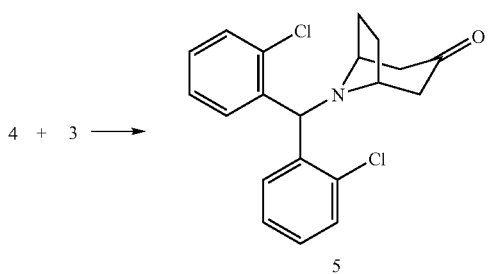

A mixture of 4 (26 g, 161 mmol), 3 (53 g, 168 mmol) and K$_2$CO$_3$ (110 g, 796 mmol) in anhydrous CH$_3$CN (410 ml) was heated at 80° C. Reaction progress was monitored by $^1$H NMR analysis. ~79% conversion was observed after 87 h. The reaction mixture was cooled to rt, diluted with CH$_2$Cl$_2$, filtered and concentrated. Purification of the residue by SiO$_2$ chromatography (4-7% EtOAc/hexane) gave the desired compound 5. $^1$H NMR (CDCl$_3$) δ 7.9 (d, 2H), 7.3 (m, 4H), 7.2 (m, 2H), 5.7 (s, 1H), 3.35 (s, br, 2H), 2.7 (dd, 2H), 2.3 (m, 2H), 2.2 (d, 2H), 1.65 (dd, 2H).

Step 5:

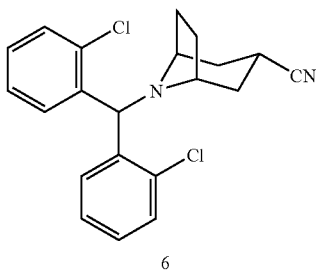

Potassium tert-butoxide (232 g) was added slowly to a stirred solution of product of Step 4 (300 g) and tosylmethyl isocyanide (211 g) in anhydrous 1,2-dimethoxyethane (3.5 l) and absolute EtOH (240 ml) under $N_2$ at $-40°$ C. The mixture was slowly warmed to rt and stirred at rt overnight. The mixture was filtered and washed with EtOAc. Most of the solvent in the filtrate was evaporated in vacuo (bath temperature <40° C.) to give a suspension which was filtered and washed with $Et_2O$ to give 6 (158 g). LC/ESI-MS m/z=371 ($C_{21}H_{20}Cl_2N_2.H^+$)

Step 6:

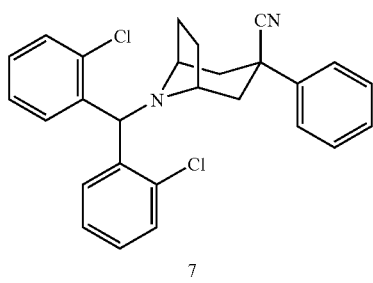

Potassium bis(trimethylsilyl)amide (0.5 M in toluene, 19.4 ml) was added to a mixture of 6 (4 g) and fluorobenzene (810 mg) at rt. The mixture was stirred at 60° C. in a sealed tube overnight, cooled to rt, quenched with saturated aq. $NH_4Cl$, extracted with EtOAc, dried over $MgSO_4$, filtered, and concentrated. Purification of the residue by $SiO_2$ chromatography (EtOAc/hexane) gave the desired compound 7. LC/ESI-MS: m/z 447 ($C_{27}H_{24}Cl_2N_2$).

Step 7:

A mixture of 7 (144 mg) and conc. $H_2SO_4$ (2 ml) was stirred at rt for 2 days. The mixture was poured into ice/$H_2O$, neutralized with NaOH pellets, and extracted with EtOAc. The organic solution was washed with aqueous $NH_4Cl$, dried over $MgSO_4$, filtered and concentrated. Purification of the residue by $SiO_2$ chromatography (0-25% EtOAc/hexane) gave the title compound. LC/ESI-MS m/z=465 ($C_{27}H_{26}Cl_2N_2OH^+$).

Efficacy in treating anxiety can be determined by assays known in the art.

Rat Conditioned Lick Suppression Assay (CLS): Water deprived CD rats (300-600 g) were trained to lick from a spout for a 0.2% saccharin solution. Daily conditioning consisted of 20 trails per day during a 10 min test session. Each trial consisted of 23 seconds unpunished drinking, following by a 7 second period signaled by a tone. The first 2 seconds of the tone were unpunished but every lick in the last 5 seconds was paired with shock delivery (0.7 mA intensity, 0.5 s duration). Once rats were conditioned to suppress the licks upon presentation of the tone then could be tested in drug studies. On test days, drug or vehicle were administered and the number of licks was recorded automatically across the 20 trial, 10 min test session with NO SHOCK presented during the conditioned, punished phase of the trial.

Rat Fear-potentiated Startle: All testing took place in the SR-LAB system (San Diego Instruments, CA) with the potentiated startle kit. Male Wistar rats (250-300 g) were conditioned to associate the presentation of a light cue with the imminent presentation of mild footshock (0.4 mA, 500 ms duration). Conditioning consisted of 20 presentations of the light/shock pairings on two consecutive days. Following conditioning, rats were tested in a FPS session that comprised on startle stimulus trials and startle stimulus trials preceded by the presentation of the conditioned light cue. Any fear associated with the light cue would present itself as an elevated response to the startle stimuli.

Guinea Pig Pups and rat pup vocalization assays: Dunkin-Hartley guinea pig pups (5-21 days) or CD rat pups (10-12 days) were removed from the dam, and administered drug or vehicle. Following a pretreatment time (during which the pups were returned to the dam), the total number of separation induced vocalizations was recorded either manually during a 5 min test for guinea pig pups, or automatically, during a 10 minute test for rat pups.

Mouse Geller-Seifter: Food restricted C57BU/6 mice were trained to lever press for a pellet on an FR-1 schedule that was progressively increased to an FR-10 schedule. After demonstrating stable FR-10 responding for a week, mice were trained on a Geller-Seifter conflict schedule. The schedule consisted on a 40 min test during which eight alternating 5 min phaes of unpunished and punished responding were presented. During the unpunished phase (house light on), the mice received a food pellet for FR-10 lever pressing. During the punished phase (house light off and signaled by a tone), the mice received a food pellet paired to foot shock delivery (0.3 mA intensity, 0.25 s duration) for FR-10 lever pressing. On test days, drug or vehicle were administered and the number of responses was recorded across a 40 min test session.

Mouse Marble Burying: Following drug treatment, male CD1 mice were placed into individual clear plastic cages containing 15 glass marbles (1.5 cm diameter) which were evenly spaced on sawdust bedding (0.5 cm deep). After 60 minutes, the mice were removed and the number of unburied marbles (less than ⅔ buried) were counted.

The activity of the compound of Example 1 was compared to the known ORL-1 agonist Ro64-6198 and to a benzodiazepine (BZDP) anxiolytic. The table below shows that the compound of Example 1 has anxiolytic-like effects comparable to benzodiazepines.

| Assay | Ex. 1 | Ro64-6198 | BZDP |
|---|---|---|---|
| Rat CLS | 3-10 mg/kg | 3-10 mg/kg | 6-10 mg/kg |
| Rat Pup USV | 10 mg/kg | 1-3 mg/kg | 1-10 mg/kg |
| GPPV | 1-3 mg/kg | 0.3-1 mg/kg | 10-30 mg/kg |
| Mouse Geller-Seifter | 30 mg/kg | 3 mg/kg | 3 mg/kg |
| Mouse Marble Burying | 30 mg/kg | — | 10 mg/kg |

Side effects of administering ORL-1 agonists are determined by the following tests:

Fixed-Ratio Responding: Food restricted rats were trained to lever press for a food reward on a FR10 schedule. The average number of lever presses per second was recorded.

Locomotor Activity: Animals were individually placed in a locomotor activity chamber for 60 min.

Rotarod: Animals were trained to a performance criterion (remain on the rotarod for 120 s at 16 RPM), 24 hours prior to the test. On testing day, animals were pretreated with drug and the time spent on the rotarod (to a maximum 120 s) was recorded at two fixed speed, 8 and 16 RPM.

Beam-Walking: Male CD rats were trained to a performance criterion to traverse a beam (2×90 cm) 24 hours prior to the test. On testing day, distance traversed was measured by a blind observer.

Compounds of the invention have improved efficacy/side-effect profiles compared to benzodiazepines.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to provide relief from anxiety. The compounds are non-toxic when administered within this dosage range.

For treating anxiety, the amount of nociceptin receptor ORL-1 agonist in a unit dose is preferably from about 0.1 mg to 1000 mg, more preferably, from about 1 mg to 300 mg. A typical recommended dosage regimen is oral administration of from 1 mg to 2000 mg/day, preferably 1 to 1000 mg/day, in two to four divided doses.

The following are examples of pharmaceutical dosage forms which contain a compound of the invention. The scope of the invention in its pharmaceutical composition aspect is not to be limited by the examples provided.

PHARMACEUTICAL DOSAGE FORM EXAMPLES

Example A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

Example B

Capsules

| No. | Ingredient | mg/capsule | mg/capsule |
|-----|------------|------------|------------|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the formula

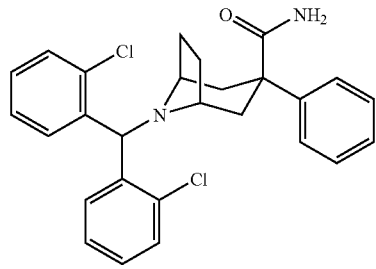

or a pharmaceutically acceptable salt or solvate thereof.

2. A pharmaceutical composition comprising a therapeutically effective amount of compound of claim 1 in combination with a pharmaceutically acceptable carrier.

3. A method of treating anxiety comprising administering an effective amount of a compound of claim 1 to a mammal or a non-mammalian species in need of such treatment.

4. The method of claim 3 wherein the mammals treated are selected from the group consisting of humans, domestic animals, livestock and wild animals, and the non-mammalian species are selected from aquatic and avian species.

* * * * *